United States Patent
Allarie et al.

(10) Patent No.: US 7,462,019 B1
(45) Date of Patent: Dec. 9, 2008

(54) IMPLANTABLE CENTRIFUGAL BLOOD PUMP WITH HYBRID MAGNETIC BEARINGS

(76) Inventors: Paul E. Allarie, 805 Emerson Dr., Charlottesville, VA (US) 22901; Gill B. Bearnson, 982 E. Jasper Cir., Salt Lake City, UT (US) 84106; Ron Flack, 4265 Viewmount Rd., Earlysville, VA (US) 22936; Pratap S. Khanwilkar, 1651 E. Shadow Cove, Salt Lake City, UT (US) 84121; B. Ajit Kumar, Suite NE. 107, 825 N. 300 West, Salt Lake City, UT (US) 84103; James W. Long, Jr., 4461 S. Parkview Dr., Salt Lake City, UT (US) 84124; Don B. Olsen, 8832 Blue Jay La., Salt Lake City, UT (US) 84121; Jeffrey Decker, 6387 Lake Trail Dr., Westerville, OH (US) 43082; Michael Baloh, 206 Greentree Park Dr., Charlottesville, VA (US) 22901

( * ) Notice: Subject to any disclaimer, the term of this patent is extended or adjusted under 35 U.S.C. 154(b) by 0 days.

(21) Appl. No.: 09/673,922

(22) PCT Filed: Apr. 22, 1999

(86) PCT No.: PCT/US99/08870

§ 371 (c)(1),
(2), (4) Date: Aug. 24, 2001

(87) PCT Pub. No.: WO99/53974

PCT Pub. Date: Oct. 28, 1999

(51) Int. Cl.
*F04B 17/03* (2006.01)
*A61M 1/10* (2006.01)

(52) U.S. Cl. .............. 417/423.12; 604/151; 623/3.14

(58) Field of Classification Search ............ 417/423.12; 604/131, 151; 623/3.13, 3.14
See application file for complete search history.

(56) References Cited

U.S. PATENT DOCUMENTS 4,135,253 A   1/1979   Reich et al.

(Continued)

FOREIGN PATENT DOCUMENTS

JP           404148095         5/1992

*Primary Examiner*—Charles G Freay
(74) *Attorney, Agent, or Firm*—Holland & Hart, LLP

(57) ABSTRACT

A pump for pumping sensitive fluids, such as blood, having no mechanical contact between the impeller and any other structure. The pump comprises a pump housing, an impeller disposed within the pump housing, a magnetic bearing system for supporting and stabilizing the impeller in five degrees of freedom, and a conformally shaped magnetically linked motor for rotating the impeller. The magnetic bearing system and motor advantageously comprise electromagnets and permanent magnets for stability and control of the impeller, and to reduce size, weight, and pump power consumption. Permanent and electromagnets are disposed on the pump housing and permanent magnets are disposed on the impeller such that by controlling electric current through the electromagnets on the housing, the magnetically suspended impeller functions as the rotor, and the housing as the stator of a D.C. motor. The system advantageously allows for sensing of relative impeller position and dynamic properties without the need for additional sensors. The fluid inlet, pump impeller, housing, and other components are configured such that flow patterns are as smooth and laminar as possible to reduce damage to the fluid, and such that eddies, flow separation, and re-circulation are reduced. In various embodiments, the pump is suitable for short or long-term implantation as a ventricular assist device or as a complete replacement heart in a human patient.

13 Claims, 15 Drawing Sheets

U.S. PATENT DOCUMENTS

| | | | |
|---|---|---|---|
| 4,589,822 A | 5/1986 | Clausen et al. | |
| 4,688,998 A * | 8/1987 | Olsen et al. | 417/356 |
| 4,880,362 A | 11/1989 | Laing et al. | |
| 5,017,103 A | 5/1991 | Dahl | |
| 5,044,897 A | 9/1991 | Dorman | |
| 5,055,005 A | 10/1991 | Kletschka | |
| 5,112,202 A | 5/1992 | Oshima et al. | |
| 5,195,877 A | 3/1993 | Kletschka | |
| 5,470,208 A * | 11/1995 | Kletschka | 417/356 |
| 5,507,629 A | 4/1996 | Jarvik | |
| 5,685,700 A | 11/1997 | Izraelev | |
| 5,840,070 A | 11/1998 | Wampler | |
| 6,074,180 A | 6/2000 | Khanwilker et al. | |
| 6,201,329 B1 * | 3/2001 | Chen | 310/90.5 |
| 6,270,831 B2 * | 8/2001 | Kumar et al. | 427/2.24 |

* cited by examiner

IMPLANTABLE CENTRIFUGAL BLOOD PUMP WITH HYBRID MAGNETIC BEARINGS

RELATED APPLICATION

The present application claims priority from U.S. nonprovisional patent application Ser. No. 09/064,352, filed Apr. 22, 1998.

BACKGROUND OF THE INVENTION

1. Field of the Invention

The present invention relates to pumps for pumping fluids such as blood that are sensitive to mechanical working or shear stress. More particularly, the present invention relates to a pump apparatus having an impeller that is magnetically suspended and rotated by electric and permanent magnets with no mechanical contact between the impeller and any other part of the pump.

2. State of the Art

There are many types of fluid pumps suitable for use in a wide range of applications, all performing the same basic function of moving fluid from one point to another, or moving a fluid from one energy level to another. However, pumps for pumping sensitive fluids, such as blood, introduce special design requirements. Additionally, pumps for implantation in a human patient for long or short-term use as ventricular assist devices (VAD's) or complete heart replacement, add additional size, weight, durability, and other requirements.

The design problems associated with sensitive fluids, including blood, generally relate to problems caused by contact of the fluid with mechanical parts and other substances present in the pump. Problem contact areas for sensitive fluids may include 1) contact with materials and structures in rotating fluid seals, 2) contact with mechanical bearing assemblies that are exposed to the fluid, and 3) use in bearing structures that depend on a layer of fluid between moving surfaces to provided reduced friction, such as hydrodynamic bearings. For example, it is well known that rotating shaft seals are notoriously susceptible to wear, failure, and even attack by some fluids. Many types of pumps may also increase mechanical working of the fluid and precipitate detrimental processes such as chemical reactions or blood clotting.

It is also well known that pumps for corrosive fluids, blood, and fluids used in food processing require careful design of the flow passages to avoid fluid damage, contamination, and other undesirable conditions. For example, ball bearing and other rolling element bearings must in general be used with some type of shaft seal to isolate the fluid from the bearing for the above mentioned cases. This may be needed to prevent damage to the bearing by caustic fluids, or to prevent damage to the fluid by the rolling elements of the bearing. For example rolling element bearings can crush and destroy the living cells in blood. Thus, rolling element bearings are generally not practical for blood pumps.

Finally, the size, weight, biocompatibility, and operating durability and reliability of blood pumps are a major concern where VAD's and heart replacement pumps are concerned. It would be desirable to have a VAD or heart replacement pump that can operate reliably for 20 or 30 years despite the normal bumping and jarring of everyday life, including unexpected impact such as from falling, yet is small enough to implant easily in a patient's chest. It is also desirable to reduce the power requirements of such a pump so as to increase mobility of the patient.

To address these problems, pumps with magnetically suspended impellers have been developed. For example, Oshima et. al. (U.S. Pat. No. 5,111,202) discloses a pump in which the impeller is magnetically suspended or levitated within the pump housing, and is magnetically, not mechanically, coupled to the pump housing. The pump employs permanent magnets rotating on a motor external to the pumping chamber, with the external permanent magnets magnetically coupled to opposing permanent magnets on the impeller. Magnetically suspended pumps are well adapted to pumping sensitive fluids because they eliminate the mechanical bearing structure or rotating seals which can damage or be damaged by the fluid.

However, such pumps that are currently known in the art present several drawbacks. First, an external motor with its own means of bearing support (ball bearings) is still required to rotate the impeller. It is the external bearing support that maintains the position of the rotor in such a pump. Though the motor is sealed from contact with blood and other bodily fluids, and is magnetically coupled to the suspended impeller, it still employs bearings which produce heat and pose the potential of failure. Naturally, such pumps tend to be bulky in part because of the size of the electric motor. These pumps are frequently unsuitable for implantation in a human patient because of size, weight, power consumption, and durability problems.

Other methods of magnetically supporting a rotating pump impeller have been developed. Olsen, et. al. (U.S. Pat. No. 4,688,998) teaches a fully suspended pump rotor employing permanent magnet rings on the rotor magnetized along the axis of rotation, and actively controlled electromagnets on the stator that create a magnetic field to stabilize the position of the rotor. This approach also leaves certain problems unsolved. While the manufacture of permanent magnets has advanced substantially, there are still significant process variations. These variations include repeatability from one magnet to the next, and homogeneity of the material within one magnet. The position and stability of the rotor in the Olsen invention is entirely dependent on the homogeneity of the permanent magnet rings. These problems are well known by designers of electro-mechanical devices, where significant steps are normally taken to reduce the dependency of device performance on homogeneous magnets. In the field of permanent magnet motors, this is a well known source of torque ripple.

It would therefore be desirable to have a pumping apparatus with a magnetically suspended impeller that is suitable for pumping blood and other sensitive fluids, and which is small, lightweight, durable, reliable, and has a low power consumption, without using an external motor to drive the impeller. It would also be desirable to have a magnetically suspended pump that has reduced sensitivity to manufacturing process variations in permanent magnets. It would also be desirable to have a magnetically suspended pump that requires no additional sensors for pump status monitoring.

OBJECTS AND SUMMARY OF THE INVENTION

It is therefore an object of the present invention to provide a pumping apparatus with a magnetically suspended impeller that is suitable for pumping blood and other sensitive fluids, by handling the fluid in a gentle manner with very low heating of the fluid.

It is another object of the present invention to provide a motor for a magnetically levitated pump impeller having a flux gap on one or both sides of the impeller that generates low attractive force between the rotor and stator relative to prior art systems.

It is another object of the present invention to provide a pumping apparatus of relatively compact size to allow implantation in the human body as either a heart assist device or as a total heart replacement.

It is another object of the present invention to provide a pump apparatus and system with parameters available for measurement that are inherently available without adding additional sensors, such as magnetic bearing current and/or motor current sensors, that can be used as an indicator of required flow and pressure when the pump is implanted in the human body, or can be used to keep the impeller controlled by the magnetic bearing.

It is still another object of the present invention to provide a pump apparatus with a long product life which requires minimal maintenance.

It is still another object of the present invention to provide a pump apparatus that can provide flow in either a constant manner or a flow that pulses on a periodic basis.

It is yet another object of the present invention to provide a pump apparatus which is configured to cause an acute change in direction of the fluid in one or more of the conduits while still handling the sensitive fluid in a gentle manner.

It is another object of the present invention to provide a blood pump in which all blood-contacting surfaces are coated with a biocompatible ceramic coating.

The above and other objects of the invention are realized in specific illustrated embodiments of an implantable centrifugal blood pump with hybrid magnetic bearings. The pump comprises a generally cylindrical pump housing, a generally cylindrical impeller disposed within the pump housing, a magnetic bearing system for supporting and stabilizing the impeller in five degrees of freedom, and a conformally shaped motor for rotating the impeller in the remaining degree of freedom, with no mechanical contact between the impeller and any other structure. The pump thus reduces damage to the fluid from the pump and damage to the pump from the fluid. The pump impeller, housing, and other components are also configured such that flow patterns are as smooth and laminar as possible, and eddies, flow separation, and re-circulation are reduced.

The magnetic bearing system and motor advantageously comprise both electromagnets and permanent magnets for stability and control of the impeller, and to reduce size, weight, and pump power consumption. The permanent and electromagnets are disposed on the pump housing and on the impeller, such that by controlling electric current through the electromagnets on the housing, the magnetically suspended impeller functions as the rotor, and the housing as the stator of a D.C. motor. A controller linked to the electromagnets allows for sensing of relative impeller position and dynamic properties without the need for additional sensors. It also allows for the adjustment of the impeller position by modification of the current flow to the electromagnets. The pump thus forms a lightweight, dependable, and compact unit suitable for short or long-term implantation as a ventricular assist device or a complete replacement heart in a human patient.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE PREFERRED EMBODIMENT

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
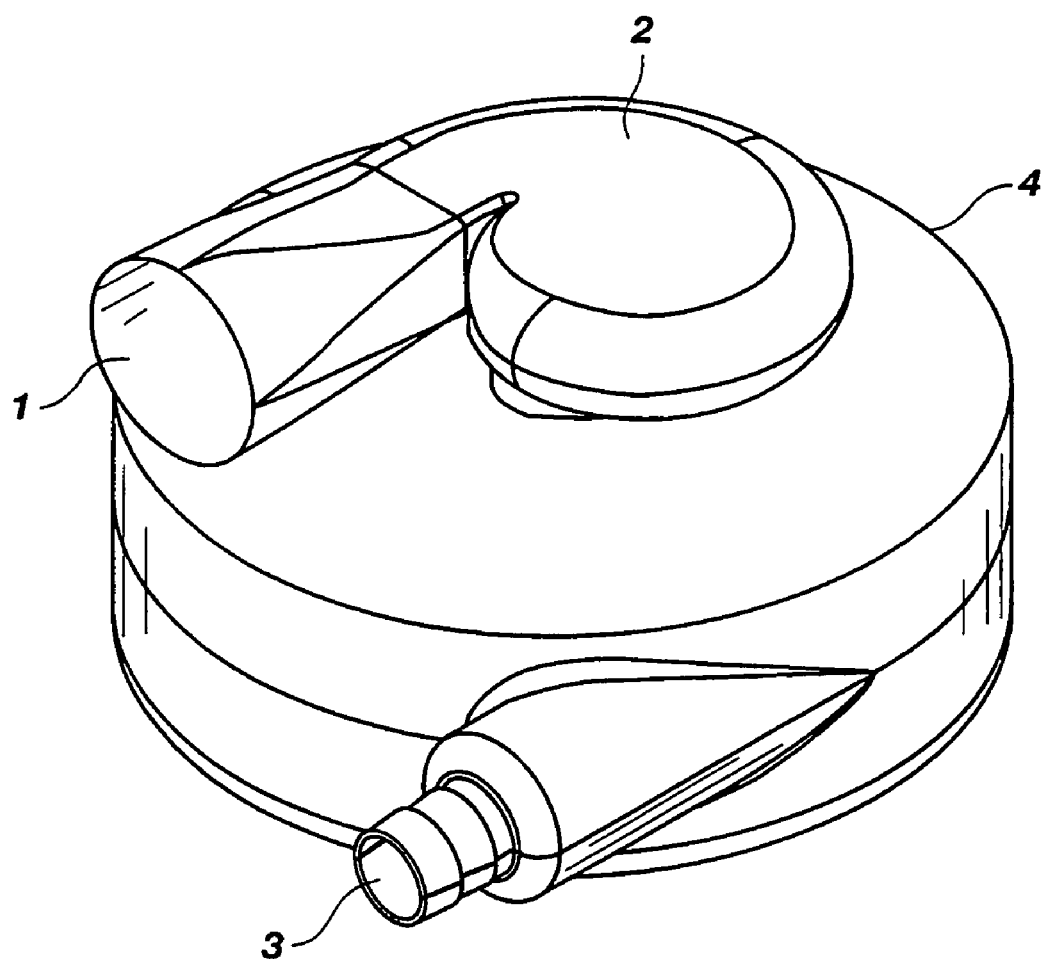
FIG. 1 shows a pictorial view of the preferred embodiment of the implantable centrifugal blood pump with hybrid magnetic bearings of the present invention.

A pictorial view of the assembled pump of the preferred embodiment is shown in FIG. 1. The pump generally comprises a housing 4 with an inlet 1, flow turning structure 2, and outlet 3. The flow turning structure 2 is configured to redirect incoming fluid flow through an acute angle in a gentle, low thermal manner using a compact structure. The turning structure is configured such that flow swirls around the inlet in a logarithmic spiral configuration, equalizing the flow rate and pressure entering the inlet. Additionally, this spiral inlet configuration reduces flow eddies and other disruptions in the flow that are detrimental to pump efficiency. The redirection of flow is thus accomplished in a gentle manner with low fluid stress that is consistent with use in a pump for sensitive fluids. A motor, magnetic bearings, and impeller are disposed inside the pump housing 4, and will be more particularly described hereafter.

Figure 2:
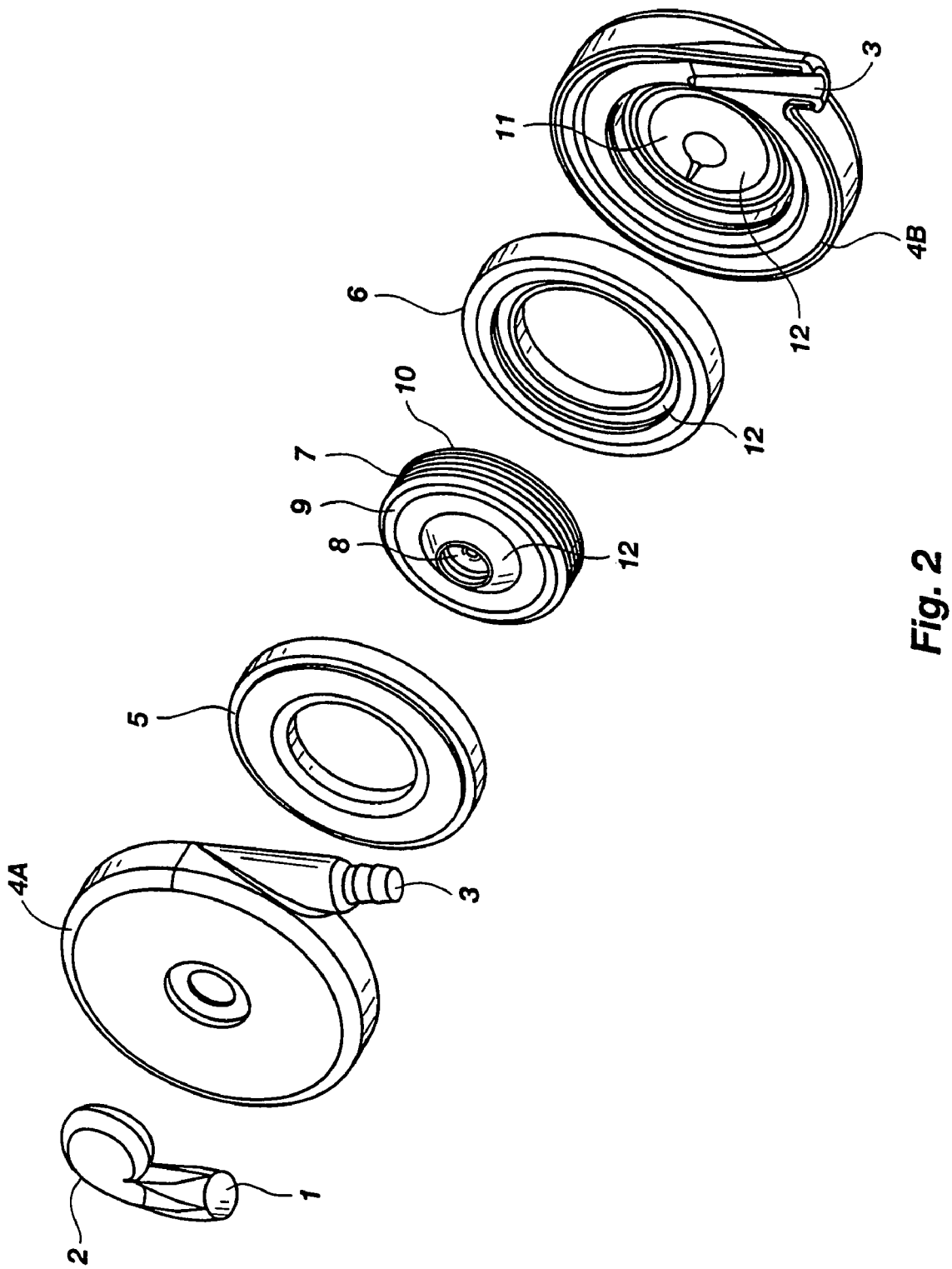
FIG. 2 provides an exploded pictorial view of the preferred blood pump of FIG. 1.

An exploded view of the assembly of the preferred embodiment is shown in FIG. 2. In this view the pump inlet 1, flow turning structure 2, and pump outlet 3 are clearly visible as in FIG. 1. This figure also shows the upper half 4A and lower half 4B of the pump housing 4. The pump further comprises an inlet side magnetic bearing actuator 5, and an outlet side magnetic bearing actuator 6. The impeller assembly 7 is disposed between the magnetic bearing actuators 5 and 6, and comprises the rotating part of the pump. The impeller 7 is designed to function as the rotor of a motor, and includes soft iron magnetic material structures 9 and 10 that act as targets on the rotor for the magnetic bearing actuators 5 and 6. These and other features of the impeller will be more apparent from the discussion of FIG. 3. The eye of the impeller 8 provides an opening for the inlet of flow into the pump vanes in the preferred embodiment. Advantageously, the motor stator 11 is incorporated in the outlet side or lower half 4B of the pump housing 4.

Figure 3:
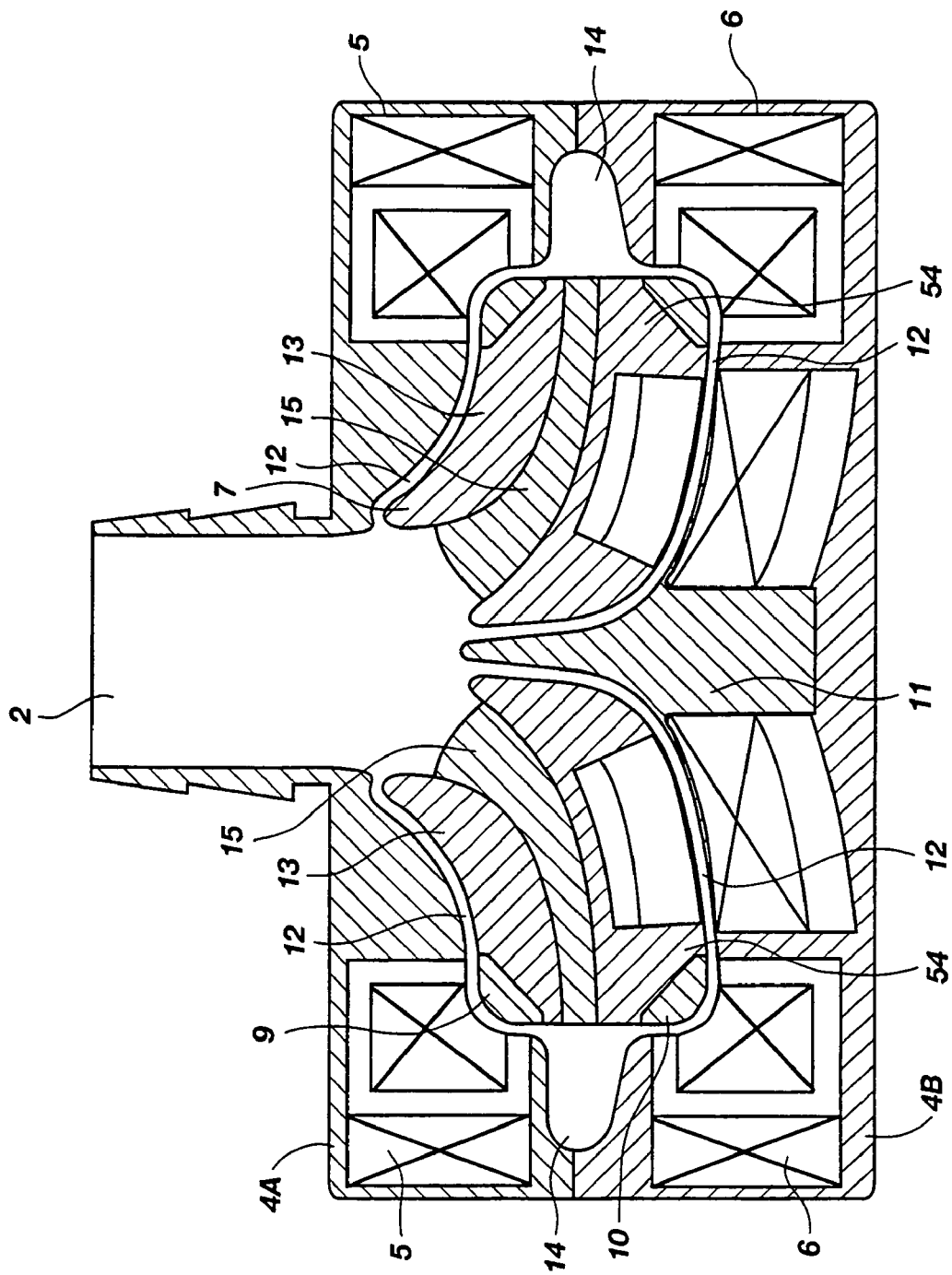
FIG. 3 provides a cross sectional view of the inner workings of the preferred embodiment pump.

FIG. 3 shows a two-dimensional cross sectional view of the inner workings of the preferred embodiment of the invention. In this view the combination of electromagnets (EM) and permanent magnets (PM) becomes visible. Advantageously, the impeller assembly 7 is the only moving part in the system, and forms a curved, conical ring disposed adjacent to the motor stator 11, and between the upper and lower bearing actuators 5 and 6. The impeller assembly 7 comprises a shroud 13 disposed above a plurality of vanes 15, and a hub 54 which supports the vanes and the elements of the motor rotor. The housing 4 is formed to provide curved fluid gaps 12 around the rotating impeller 7. The gaps 12 are configured to work in conjunction with the impeller 7 to accommodate flow without damaging blood or other sensitive fluids. This is accomplished by making the flow passage clearances 12 short in length, yet with large bending radii to allow gentle backflow around the shroud 13 and hub 54.

The vanes 15 of the impeller 7 drive the fluid from adjacent the inlet 2 into the pump volute 14, which is formed around the perimeter of the inner space of the housing 4. The volute 14 is formed in a logarithmic spiral shape, more evident in FIG. 2, which spirals out from the center of the pump, gathering the flow from the impeller vanes 15, and directing it to the tangentially aligned outlet 3 (FIG. 1). This configuration adds to the advantages of the invention through minimizing damage to blood or other sensitive fluids by gradually redirecting the flow across the vanes 15 from the inflow 2 to the pump volute 14, where the flow is then directed to the outlet 3.

As depicted in FIG. 3, the fluid gaps 12 in the pump are advantageously configured to accommodate sensitive fluid flow by being short in length and arcuate in shape with large bending radii to minimize sharp turns in the flow passages. This design also helps to reduce potential stagnation and shear of the fluid. Notably, the gap 12 between the rotating impeller 7 and the stationary housing in the vicinity of the motor 11 is neither radial nor axial as in conventional motor designs, but is conformally shaped to accommodate the particular requirements of the flow paths and the motor design. By virtue of its conformal shape, the curved upper surface of the motor 11 advantageously provides an axial force on the impeller/rotor 7, while simultaneously powering its rotation.

As shown, the arcuate flow passageways 12 are thus integrated directly into the motor design, as will be described in more detail below. This integrated approach of motor design with pump design is not reflected in prior art pumps. It will be apparent that the invention is not restricted to the motor shape shown in this or other figures, but may be otherwise configured and still provide the advantages of conformal design. The same approach to motor design and fabrication can be employed to make a variety of motors with conformally shaped gaps between the rotating and stationary parts.

Figure 4:
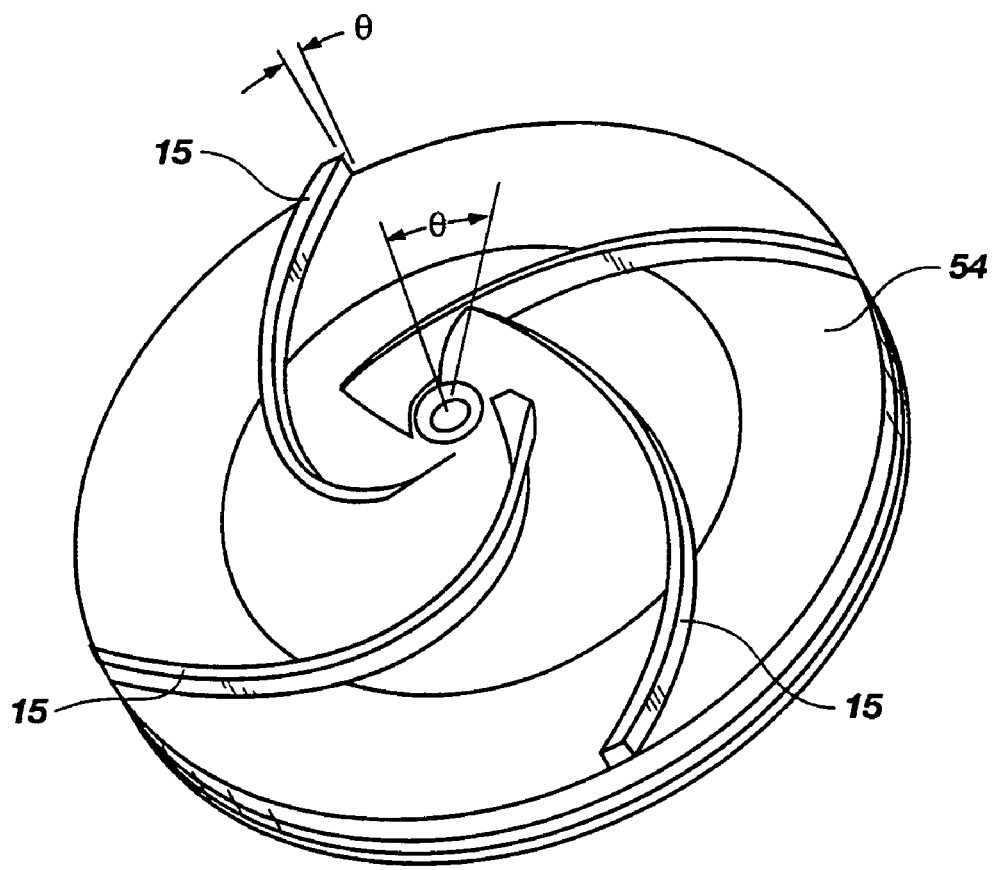
FIG. 4 shows a three-dimensional view of the pump impeller with the vane shroud removed.

FIG. 4 shows a pictorial view of the impeller 7 with the vane shroud 13 removed. In this view the plurality of arcuate vanes or blades 15 are clearly visible. The impeller vane layout is designed to provide a smooth transition from the inlet blade angle to the discharge blade angle. It will be apparent from this figure that the inlet blade angle $\theta$ varies continuously from hub to shroud, with a greater angle $\theta$ near the inlet 2, and an angle approaching zero near the outlet (measured relative to a line perpendicular to the plane of the impeller), to reduce the incidence of flow angles over the entire blade length.

The pump intentionally allows relatively high leakage flows in the gaps 12 at the shroud side of the impeller, and along the hub side of the impeller. Relatively large fluid gaps are desirable on both the inlet side and discharge side of the impeller to allow for recirculating flows in the gaps at low shear stress levels. As will be appreciated, the acceptable level of shear is a function of expected cell transit time through the gap. However, for both magnetic bearing and motor design considerations, it is desirable to minimize the size of the flux gap. To balance these opposing factors, the inventors have experimented with gaps of various sizes, and have determined that a gap of 0.015 inches (15 mils) is presently preferred. However, it will be apparent that other gap sizes, such as 10, 20, and 30 mils may also be found suitable, and the inventors anticipate further study of these options using flow visualization.

Figure 5C:
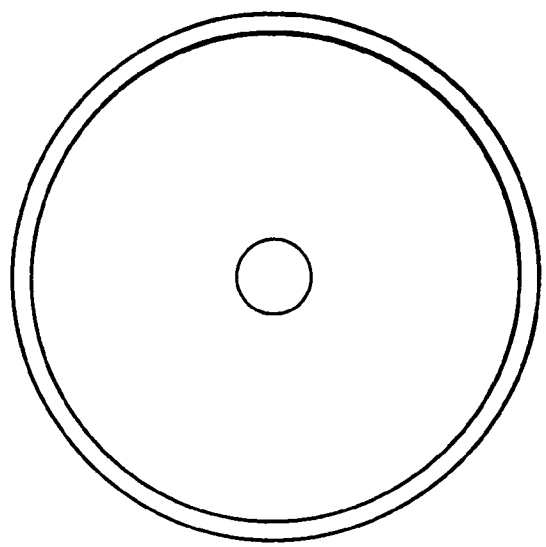
FIG. 5C provides a view of the back of the pump motor assembly.
Figure 5B:
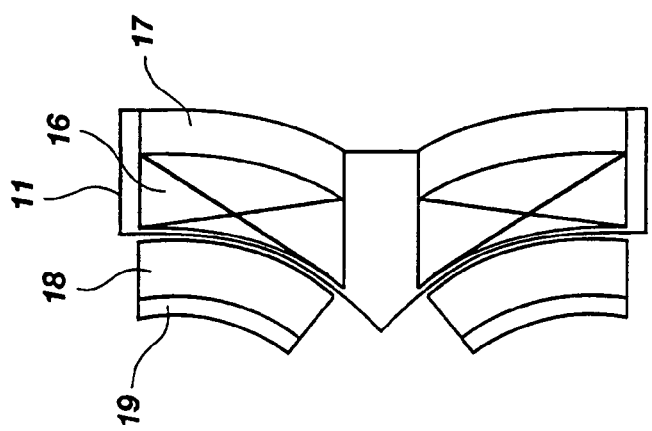
FIG. 5B is a cross sectional view of the pump motor assembly.
Figure 5A:
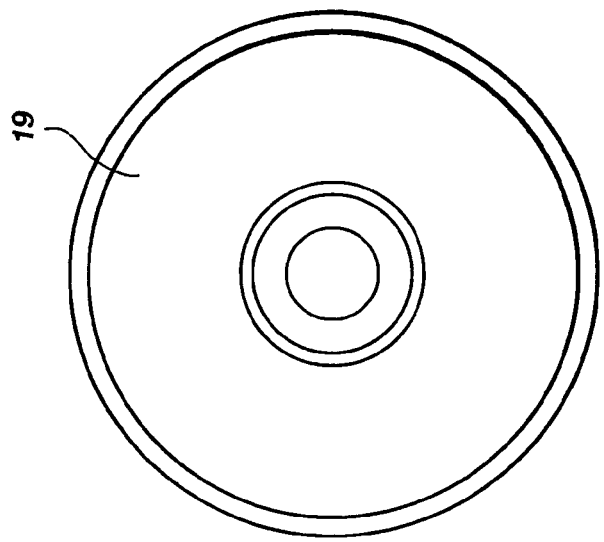
FIG. 5A is a view of the front of the pump motor assembly.

FIG. 5B shows a two-dimensional cross sectional view of the motor assembly, and FIGS. 5A and 5C are front and back views of the same. The motor stator assembly 11 comprises motor coils 16 having a nonmagnetic core, backed by a backing material 17, preferably a soft iron magnetic material which may be laminated or not. Alternatively the backing material 17 may be formed of a non magnetic material depending on the level of constant force desired between the rotor and stator. In the preferred embodiment, the backing material 17 is laminated soft iron material. The impeller/rotor 7 also comprises a ring permanent magnets 18, preferably backed by a soft iron backing material 19, which acts as a magnetic yoke for the permanent magnets 18. The soft iron backing 19 improves performance, but is not required for the invention to function.

Figure 6C:
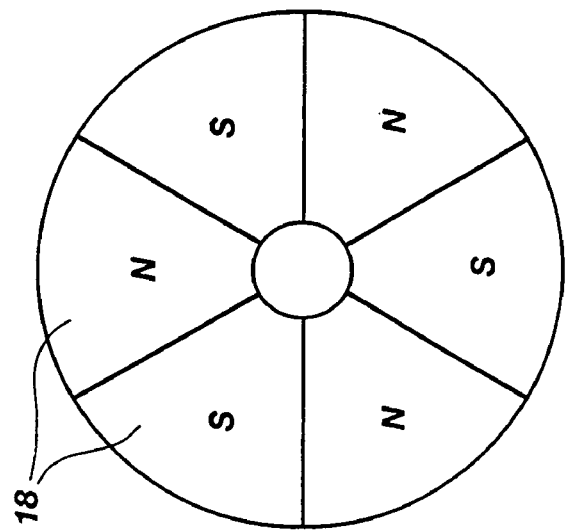
FIG. 6C depicts the polarity of the permanent magnets on the motor rotor in one embodiment.
Figure 6B:
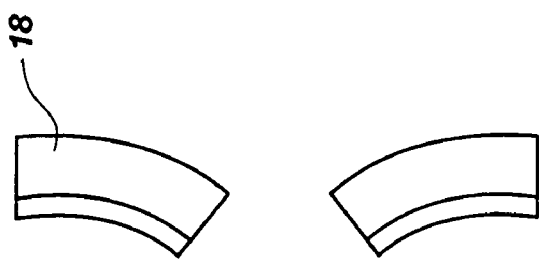
FIG. 6B is a cross sectional view of the motor rotor assembly.
Figure 6A:
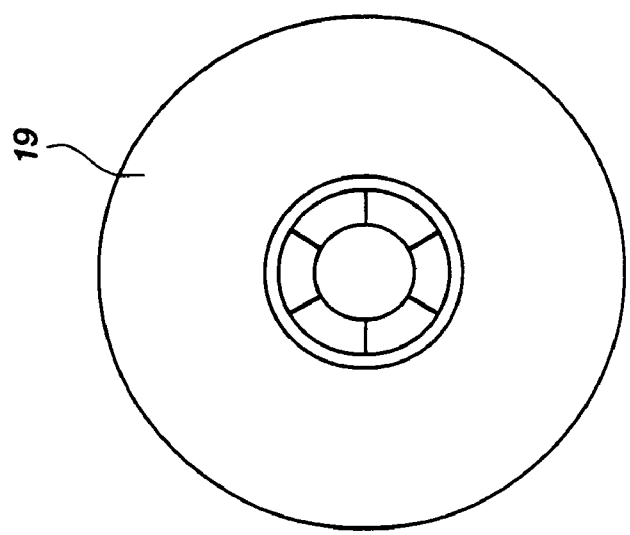
FIG. 6A is a view of the front of the motor rotor assembly.

FIGS. 6A-6C provide detailed views of the motor rotor assembly. Permanent magnets 18 are arranged around the circumference of the rotor 7 in alternating polarity configuration, shown in FIG. 6 by the common designations N and S. As will be appreciated, in order to provide magnetic flux across the flux gap, the magnetization of the permanent magnets 18 is perpendicular to the flux gap. In FIG. 6, the flux of the permanent magnets can be visualized as flowing into or out of the plane of the page. The preferred embodiment as shown comprises 6 magnets, but the invention can be implemented with any even number of magnets, such as 4, 6, 8, etc.

Figure 7C:
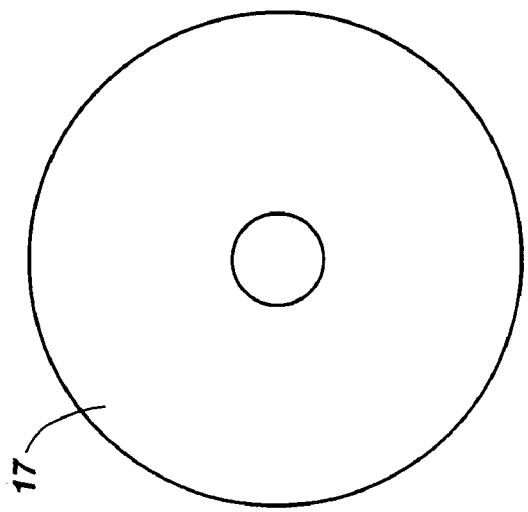
FIG. 7C is a view of the back of the stator.
Figure 7B:
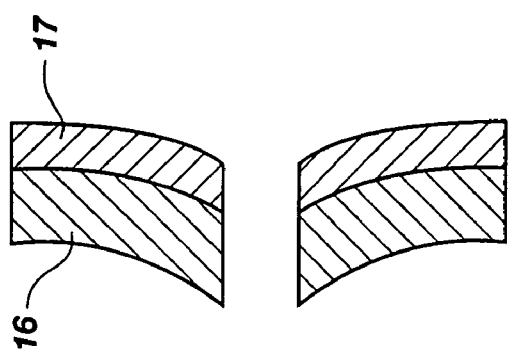
FIG. 7B is a cross sectional view of the stator.
Figure 7A:
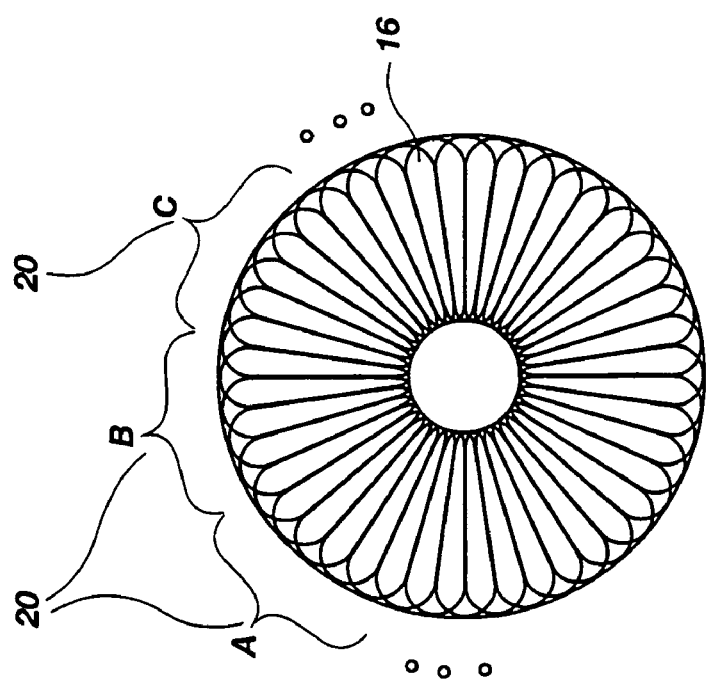
FIG. 7A is a detailed front view of the motor coils on the stator.

FIGS. 7A-7C show detailed views of the motor coils 16 and stator soft iron backing 17. The coils 16 are separated into a plurality of discrete stator poles 20. The number of stator poles must be divisible by the number of phases, which can be 2, 3, 4, or more. For example, in the embodiment shown, the designated stator poles (depicting one third of the stator circumference) are labeled A, B, and C because the preferred pump is designed to function on 3-phase electrical power. Nine poles are thus provided, but any number that is divisible by 3 could be used with 3-phase power.

This approach to motor design has several advantages. First, the fluid/flux gap between the rotor and stator is conformally shaped to the requirements of the fluid flow path 12 as discussed above. Second, the motor is highly efficient due to the balance of the amount of permanent magnet material with the volume of coils and soft iron. Third, the motor can be constructed in such a way that it only generates rotational forces or generates primarily rotational forces. This is a very important advantage in a system that uses magnetic bearings, since the size and power level of the magnetic bearings depends on the magnitude of the forces other than rotational force generated by the motor. Prior art integrated pump designs for sensitive fluids do not use this approach. Additionally, this motor is a slotless motor because the coils do not comprise a magnetic core, and the magnetic material 17 is thus separated from the permanent magnets in the rotor by the dimension of the coils 16.

The support of the rotating impeller requires control of five degrees of freedom: 3 translations (x,y,z) and 2 angular displacements ($q_x$ and $q_y$). There are several types of forces which act upon the impeller: fluid forces, gravitational forces, and dynamic forces. The fluid forces are due to fluid pressures acting on the impeller and the changes in momentum as the flow direction is changed. The gravitational force (vertically downward) is due to the difference between the weight of the impeller and the buoyant force, in blood, acting on the impeller in different orientations, depending on the orientation of the body relative to the vertical. Dynamic forces act upon the impeller due to bodily accelerations during such activities as sudden motions, impact after a fall, etc.

The hybrid integrated EM/PM bearing of the present invention uses flux from both an electromagnetic flux source and a permanent magnetic flux source in the same integrated multiple pole configurations to control the five degrees of freedom. The permanent magnet (PM) circuit is integrated into a ring configuration with the electromagnet (EM) soft iron magnetic circuits, the EM coils, the magnet target, and a saturation link.

Figure 8:
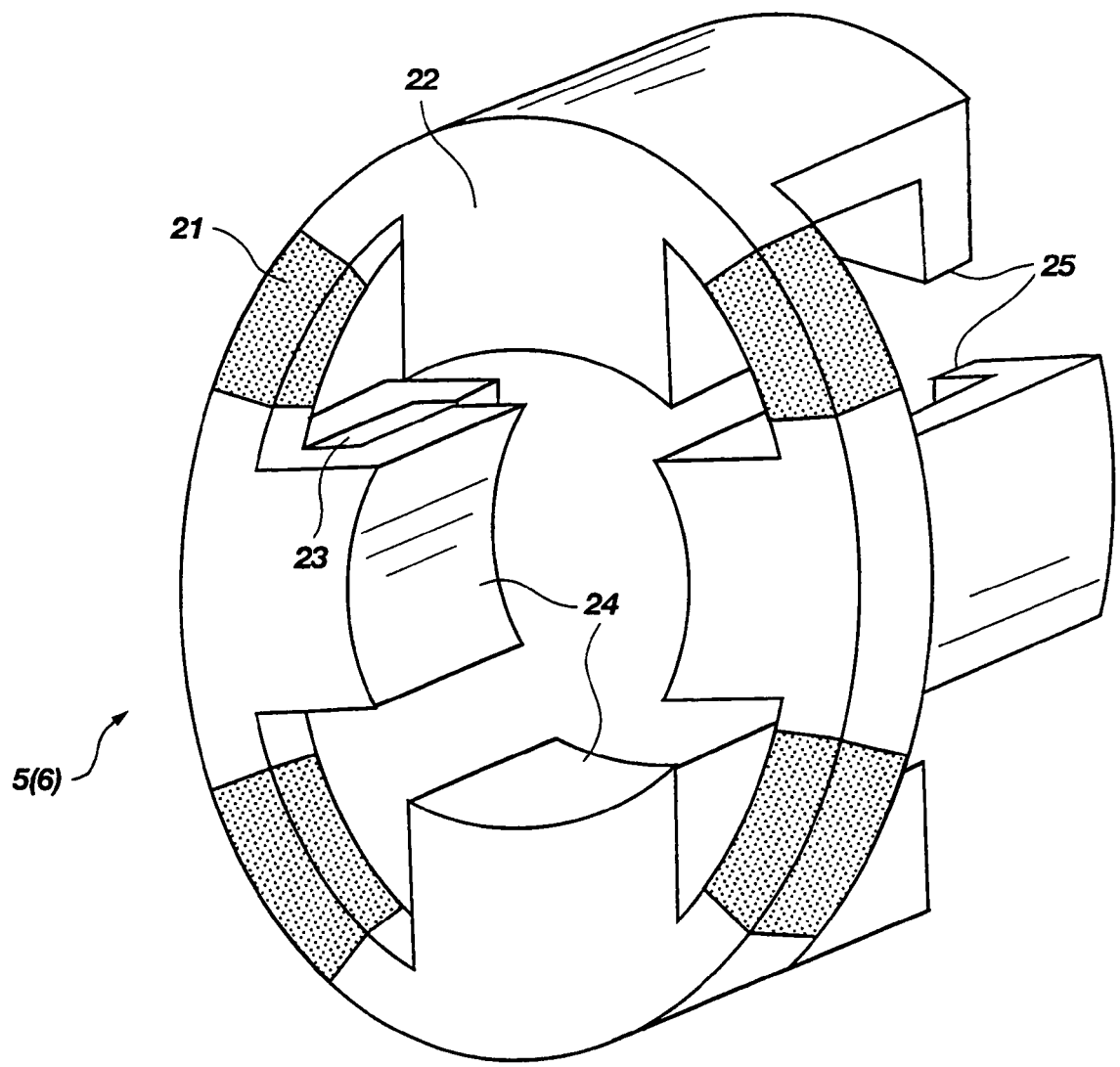
FIG. 8 is a pictorial view of a hybrid EM/PM magnetic bearing ring.

FIG. 8 shows a pictorial view of the preferred embodiment of a bearing actuator 5 (or 6) with permanent magnets 21 and soft magnet poles 22. FIG. 8 is intended to illustrate the magnetic materials only—no coils are shown in FIG. 8. A slot 23 for accommodating one of the coils is designated for reference. FIG. 8 depicts an actuator having four poles 22, which is preferred, but any other even number of poles, i.e. 6, 8, or more, may be advantageously employed in the present invention. Each pole 22 includes a thrust bearing pole 24, for providing axially oriented magnetic flux in the gap between rotor and stator, and a radial bearing pole 25, for providing radially oriented magnetic flux in the gap between rotor and stator.

In the present invention, two actuators (5 and 6) as depicted in FIG. 8 are employed: one on the inlet side of the impeller and one on the discharge side. These rings may be identical in construction, such that the PM flux is equal in both rings, or different so that the PM flux in one ring may be larger than in the other ring. The PM flux serves as the constant magnetomotive force (MMF) in the flux loops, and functions as the bias flux acting throughout the magnetic circuits. It is well known in magnetic bearing design that a bias flux in the soft iron electromagnets is useful to linearize the response of the actuators and to provide increased dynamic force load capacity.

Figure 9:
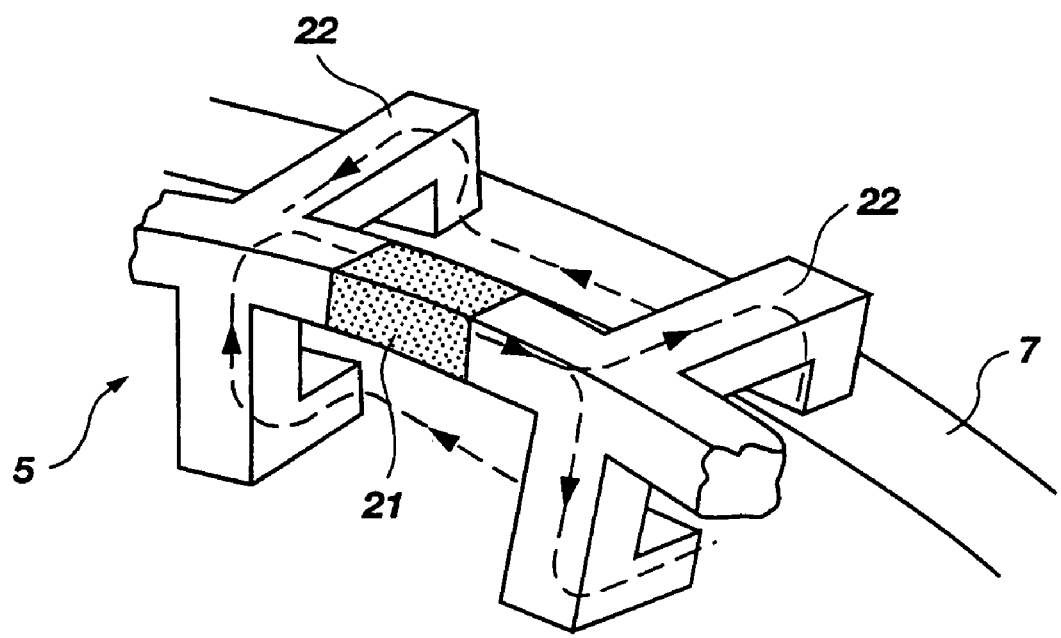
FIG. 9 is a cutaway view of part of a hybrid EM/PM magnetic bearing ring showing the flux paths for one permanent magnet.

FIG. 9 shows the flux paths for one permanent magnet 21. The permanent magnet 21 is disposed between the axial and radial flux paths of two electromagnet poles 22 in the actuator 5, and supplies permanent magnetic flux to the electromagnet poles on either flux path to provide dynamic force load capacity (also known as slew rate capability). Dynamic force load capacity is a measure of the ability of the magnetic suspension system to change force within a short period of time to control the rotor position. In prior art electromagnetic bearings, this bias flux is typically provided by a bias current through the EM bearing coils, with a resulting much higher steady state power loss.

Blood and other fluids that are sensitive to heating are easily accommodated by this invention, because the innovative magnetic bearing design reduces power dissipated in the magnetic bearings as compared to prior art systems. This is accomplished, in part, by the use of permanent magnets. While permanent magnets have been employed in some prior art blood pumps, the embodiments in this invention present advantages in terms of 1) size of the magnetic bearing system, 2) bearing stiffness achieved in this configuration of the permanent magnets, and 3) power dissipated in the magnetic bearings.

Figure 10:
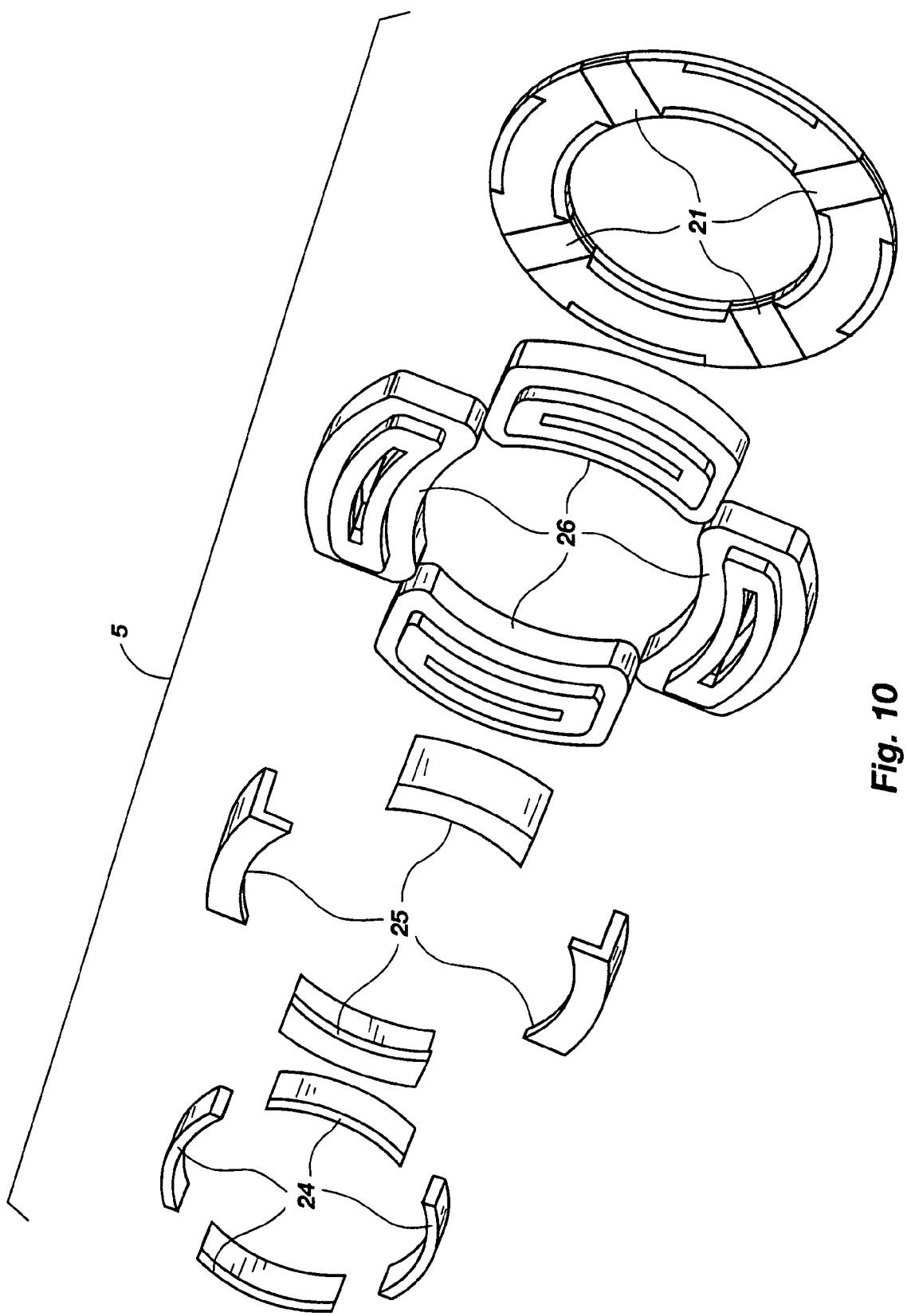
FIG. 10 depicts a preferred embodiment of the magnetic suspension actuator similar to FIG. 9, but including the coils.

FIG. 10 shows an exploded view of a preferred embodiment of the magnetic suspension actuator 5 similar to FIG. 9, but including coils 26, and shown in an orientation inverted from FIG. 8. The PM flux is directly integrated into a multiple pole ring configuration with the EM flux. Wire coils 26 suitable for providing, a MMF in the EM section of the ring configuration are included in the construction. The radial and axial gap fluxes are varied with the EM flux, where the EM flux is adjusted by the coil currents to control the impeller position. The bearings have two EM flux paths: one that has a path including a radially oriented flux gap, and another containing an axially oriented flux gap. Both of these flux paths have a combination of EM and PM flux existing in them.

Figure 11:
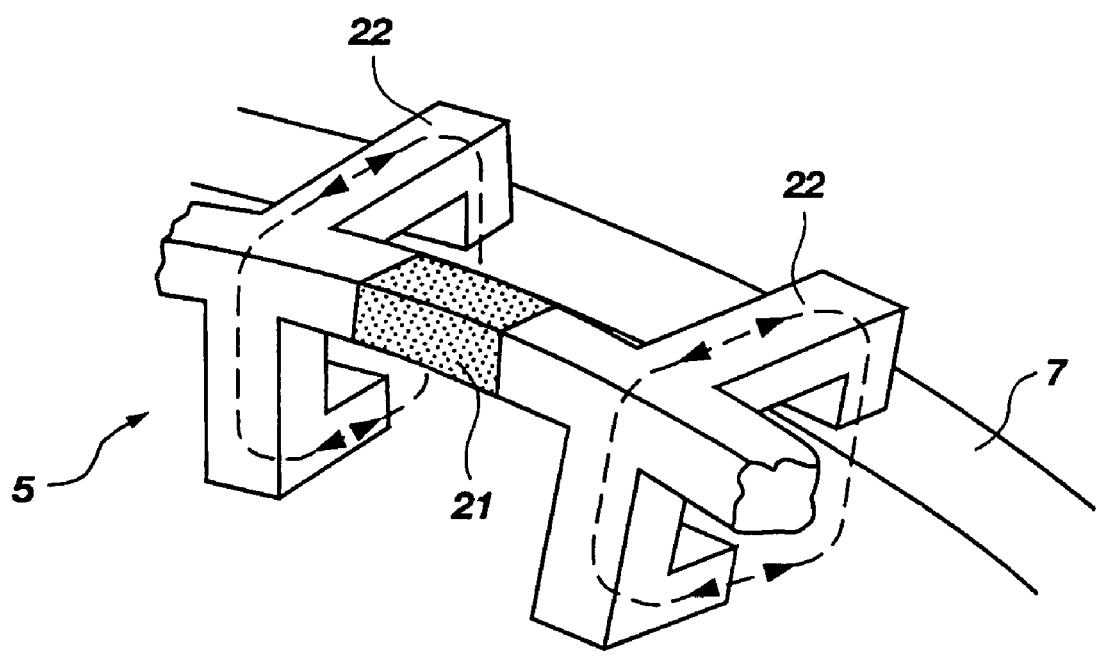
FIG. 11 is a cutaway view of part of a hybrid EM/PM magnetic bearing ring showing the flux paths for two electromagnets.

FIG. 11 shows the EM flux paths. When it is desired to increase the magnetic flux in the air gap to increase the force acting on the impeller target, the corresponding coil current is increased the necessary amount. Alternatively when it is desired to decrease the magnetic flux in the air gap to decrease the force acting on the impeller target, the corresponding coil current is decreased the necessary amount or driven in the opposite direction. The presence of a permanent magnet directly in the EM flux path would create very high magnetic reluctance in that path. Hence, the structure is set up such that the EM flux path does not include any permanent magnets, but the EM and PM flux paths are combined at the gap.

The control (EM) flux flows from the stator through an air gap at one pole to a soft iron target mounted on the impeller and leaves the target to return to the stator through another pole. For example, the control (EM) flux may flow out of the stator to the target in a radial air gap and then return to the stator via the axial air gap. Thus at any given time, the control current activates the flux in a manner such that the overall flux is increasing in one of the air gaps but decreasing in the other.

Figure 12:
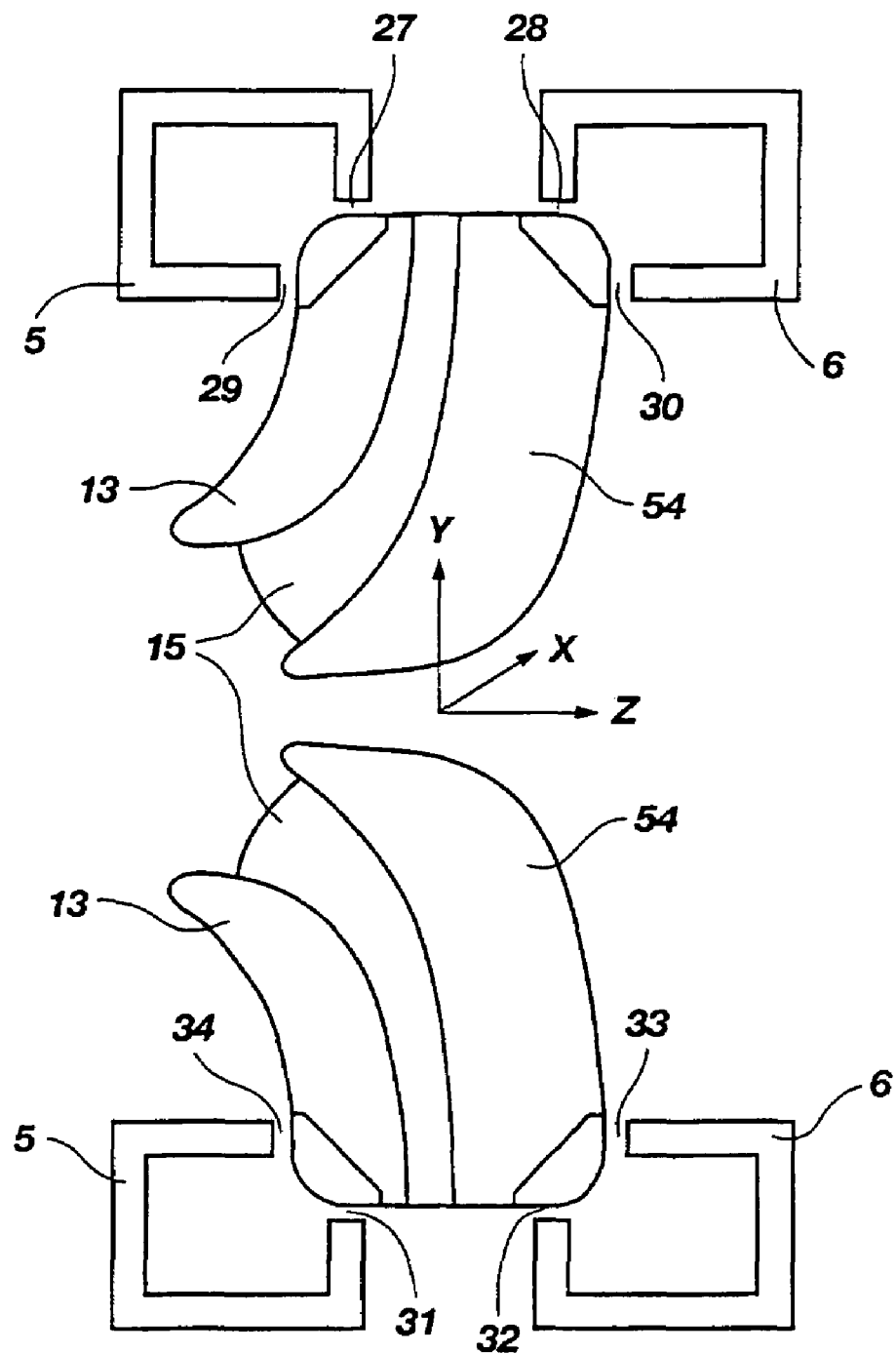
FIG. 12 shows an exploded pictorial view of the four bearing sets of poles, air gaps, and targets.

The actions of the air gap fluxes are coordinated to independently control the radial and axial centering forces without coupling between the two directions which simplifies the controller algorithm greatly, as compared to the fully coupled case. FIG. 12 is used to illustrate the control method in a two-dimensional version of the integrated hybrid EM/PM magnetic bearing system. There are four sets of bearing poles, air gaps, and targets shown in cross section in FIG. 12, including two inlet side radial flux gaps 27 and 31, two discharge side radial flux gaps 28 and 32, two inlet side axial flux gaps 29 and 34, and two discharge side axial flux gaps 30 and 33.

There are four major components in a typical prior art magnetically suspended pump control system: an actuator, a controller, a power amplifier, and proximity sensor(s) to measure the position of the impeller. Since a fully permanent magnetic suspension is not possible, every magnetic suspension system must include some means of active control. The control algorithm configured for use with the present invention operates as follows. To move the rotor in the positive Y direction (radial), it is necessary to produce a radial force, but not simultaneously produce an axial force, so as to keep the impeller/rotor in the centered position. The EM coils in the top of the rotor are activated so that the magnetic flux in the inlet side axial flux gap 29 and discharge side axial flux gaps 30 is increased equally and activate the other top EM coils so that the flux in the inlet side radial flux gap 27 and discharge side radial flux gap 28 are decreased equally. The coils in the bottom of the rotor are activated so that the flux in the inlet side radial flux gap 31 and discharge side radial flux gap 32 are increased equally and activate the other EM coils so that the flux in the inlet side axial flux gap 34 and discharge side axial flux gaps 33 are decreased equally. This combination produces a net radial force downward, opposite to the upward motion of the rotor, and no net axial force: Reversing this combination creates a net upward force if the impeller moves downward. A similar combination of EM coil currents produces a net axial force or moments about the x or y axes without any radial force. If the inlet and discharge side rings are not identical, a relatively simple control algorithm, based on the differing pole face areas and flux levels, is used to decouple the forces and moments generated to center the impeller/rotor.

Figure 13:
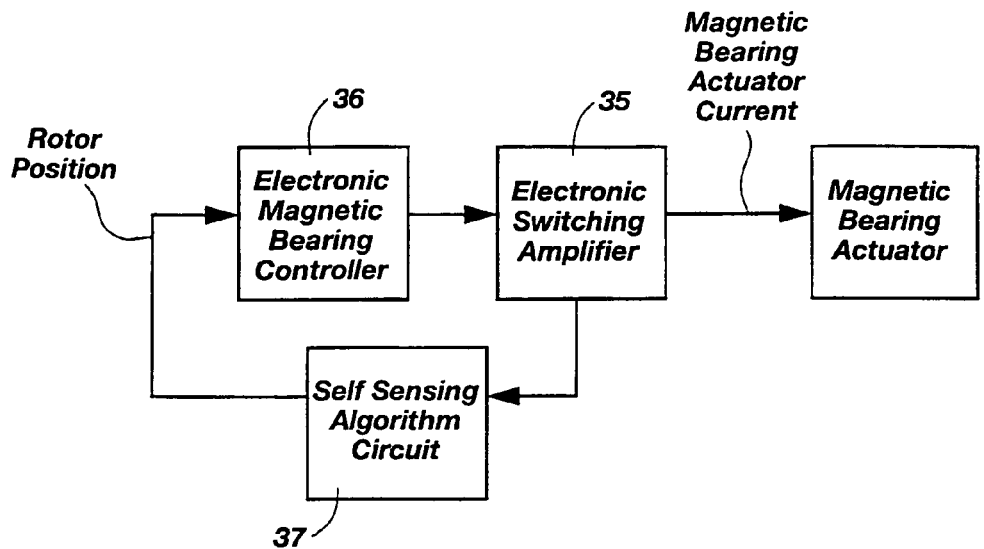
FIG. 13 shows a block diagram of an electronic controller for providing control of the magnetic bearing actuator.

The magnetic bearing actuator is controlled by an electronic controller 36, which is included in the block diagram of FIG. 13. Conventional magnetic bearings require physical sensors to provide feedback control signal to a controller. However, in the present invention, there are no physical sensors employed. Instead, the controller 36 constantly monitors and evaluates the impeller position by means of a passive self-sensing system. The position of the rotor is measured using a self-sensing algorithm, which employs feedback from the switching amplifier 35. The switching amplifier 35 receives an input signal from the controller 36 indicating the average value of current required for each coil. The switching amplifier then adjusts the average value of the coil current using pulse-width-modulation, or some other switching approach.

The controller system of FIG. 13 comprises an electronic self-sensing circuit 37, which implements the algorithm previously described. The self-sensing circuit 37 employs the characteristics of the actuators themselves in sensing the position of the rotor. It is well known that inductance or flux in a coil with a soft iron core changes with the magnetic flux linkage in the coil. In the magnetic circuit in FIG. 11 it can be easily seen that the flux linkage in the coil depends on the gap between the coil and the soft iron material in the stator, and the soft iron material in the rotor. Hence, the inductance in the coil changes when the position of the rotor changes within the pumping cavity. As the inductance of the coil changes, the time constant of the switching waveforms in the switching amplifier change as well. A combination of electronic filters and a feedback controller circuit are used to remove switching current variations in the switching amplifier signals. Thus the physical gap between the housing 4 and impeller 7 is directly related to the coil currents in the magnetic actuator, and the position of the impeller/rotor can be constantly monitored by virtue of this characteristic without the need for additional sensors.

The magnetic bearing actuator is controlled by adjusting the EM coil currents and creating magnetic forces needed to center the impeller. The control algorithm is a feedback controller employing a signal correlated with the translational displacements of the impeller in three directions and two angular displacements in two axes perpendicular to the motor spin axis, represented as x(t). The controller operates on a mathematical model of the magnetic bearing geometry and magnetic properties including both the EM and PM flux paths, the electrical properties of the bearing EM coils, the properties of the power amplifiers, properties of the preamplifiers, and the translational and angular displacement sensing circuits.

The controller algorithm may consist of a proportional-integer-derivative controller, where the control signal G(t) has three components: 1) proportional to the translational or angular displacements with constant $K_p$, 2) proportional to the time integral of the translational or angular displacements with constant $K_i$, and 3) proportional to the translational or angular velocity of the form with constant $K_d$.

$$G(t) = K_p x(t) + K_i \int x(t)dt + K_d \frac{dx(t)}{dt}$$

Alternatively, the controller may take the form of mu synthesis, or similar controller, for a controller where feedback is used and the controller is able to take into account uncertainties in the mathematical model of the system. Another possible controller algorithm is the use of a sliding mode (variable structure control) which employs a reaching condition to place the impeller translational displacements and angular displacements on a hyperplane (sliding surface in phase space), known to practitioners of the art, and create a condition where the impeller states are moved along the hyperplane. The controller currents are switched on when the impeller position moves off of the sliding surface to return it to the sliding surface, and switched off when the impeller returns to the desired surface. This type of controller includes non-linear effects and the capability to adapt to uncertainty in the applied forces acting on the impeller, such as fluid forces.

A means is provided where the determination of the impeller translational and angular displacements is performed with electronic devices rather than a physical sensor, such as an eddy current or inductive sensor. The magnetic bearings will have the coil currents supplied by switching power amplifiers operating at a high frequency such as 20 kHz. The approach here is to use both the low frequency component and high frequency components of the coil currents to determine the resistive and inductive properties of the coil. The low frequency current is obtained from electronic means which measure the instantaneous control currents following use of a low pass filter. The high frequency current is obtained from an electronic measure of the instantaneous envelope of the switched coil currents and a high pass filter. The inductive property of the coil is related to both the coil current and the air gap length. This information is combined with other available knowledge of the switching amplifier duty cycle to evaluate the air gap length, but separating the effect of the changes in coil inductance due to controller currents from the change in inductance due to the change in air gap length. The air gap lengths are evaluated using a direct method of evaluating these properties. Alternatively, if there are errors in the air gap values using the direct method, a feedback loop is used with a parameter estimation algorithm to converge to a closed loop value of the air gap.

Figure 14:
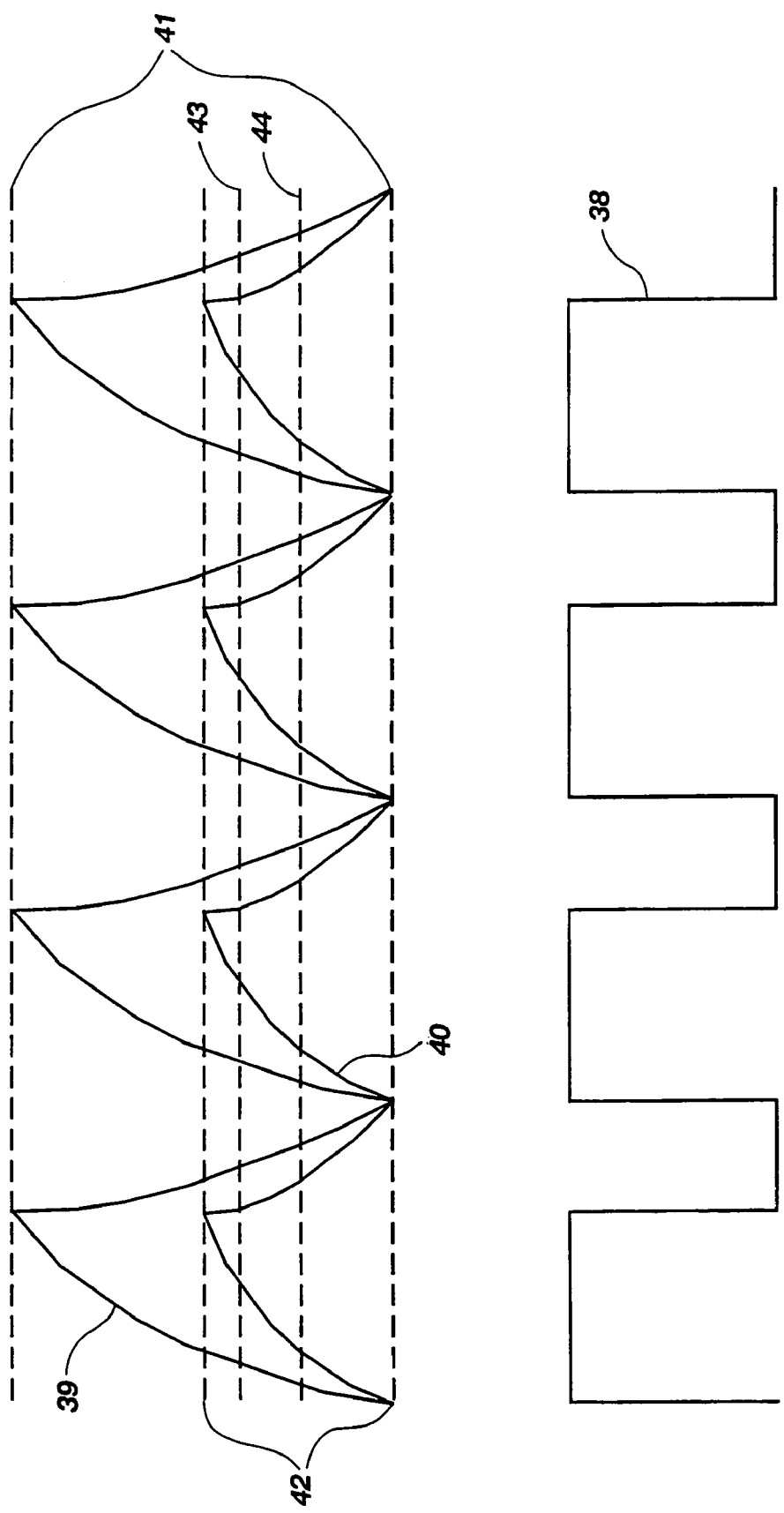
FIG. 14 shows a representative applied voltage waveform and resulting representative current waveforms for two different positions of the rotating impeller.

There are several advantages to this approach. First, the physical size of the pump can be reduced because there is no space required for sensors. Second, physical sensors are potential points of failure and the passive electronic sensing system should be more reliable. Third, the number of wires coming off of the heart pump is significantly less. As an illustration of the self-sensing concept. FIG. 14 shows an applied voltage waveform 38 and the resulting current waveforms for two different positions of the rotating impeller. The current for position 1 is denoted at 39, and the current for position 2 is denoted at 40. The overall envelope of the position 1 current is denoted at 41, and the envelope for the position 2 current is denoted at 42. Average currents for position 1 and position 2 are denoted at 43 and 44 respectively.

Figure 15:
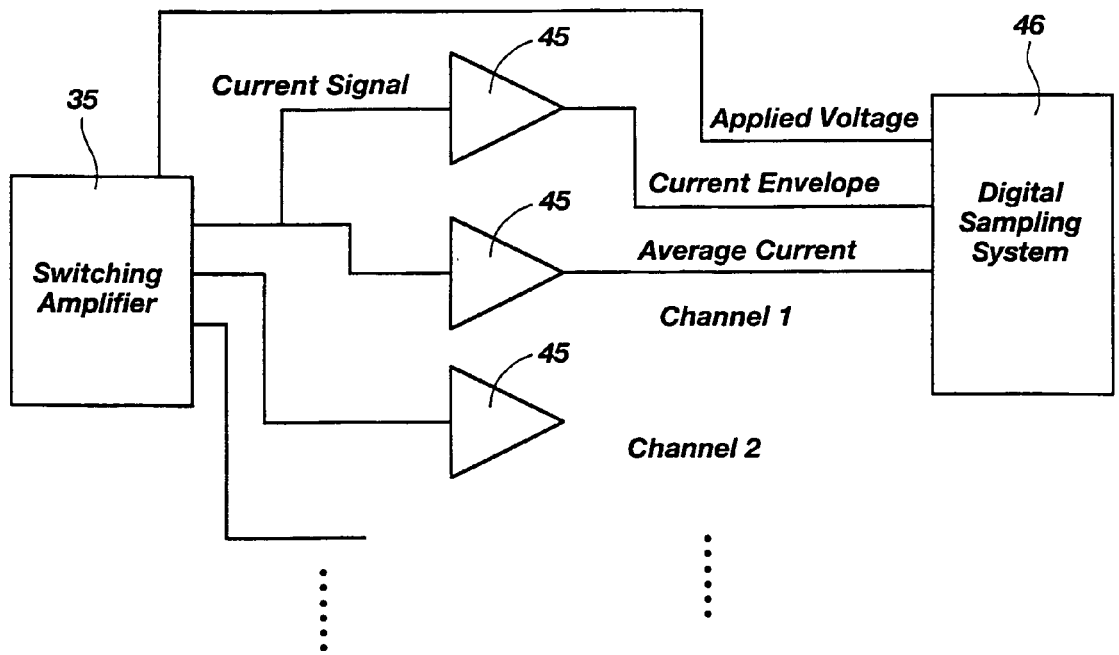
FIG. 15 shows one implementation of the self-sensing electronic circuit.

FIG. 15 shows the implementation of the self-sensing electronic circuit 37. Filters 45 operate on the current signal obtained from the switching amplifier 35, resulting in the envelope and average value waveforms. The envelope, average value, and applied voltage are fed into the digital sampling system 46 where the variation in current waveform envelope relative to the average current and the applied voltage is used to determine the electrical time constant of the resistance-inductance circuit in the actuator. From this information, the inductance, and hence the rotor position can be derived. An alternative approach is to sample the current waveform directly. The approach of this invention thus provides the significant advantage of lowering the required sampling rate of the digital sampling system significantly, while still obtaining all of the necessary information from the waveforms.

This sensing approach eliminates the separate position sensors used in prior art systems with the following advantages: 1) smaller system size 2) improved reliability due to decrease number of components, 3) reduced wire count. Additionally, envelope and average values of the current and voltage signals are used to reduce digital sampling requirements, thereby significantly reducing complexity and cost of the system.

One significant concern with the use of permanent magnets and permanent magnet biasing is the force developed when the EM coil currents are turned off and the impeller is off center, against one of the walls. The PM circuits have lower reluctance on the side where the flux gaps are zero, with resulting high forces, and much higher reluctance on the sides where the flux gaps are large, with resulting lower forces. This high, new, off-center force, called the lift-off force, must be overcome to initially center the impeller by the EM control fluxes. If no suitable design is employed, this force is large and corresponding large EM coils and control currents will be required.

Figure 16:
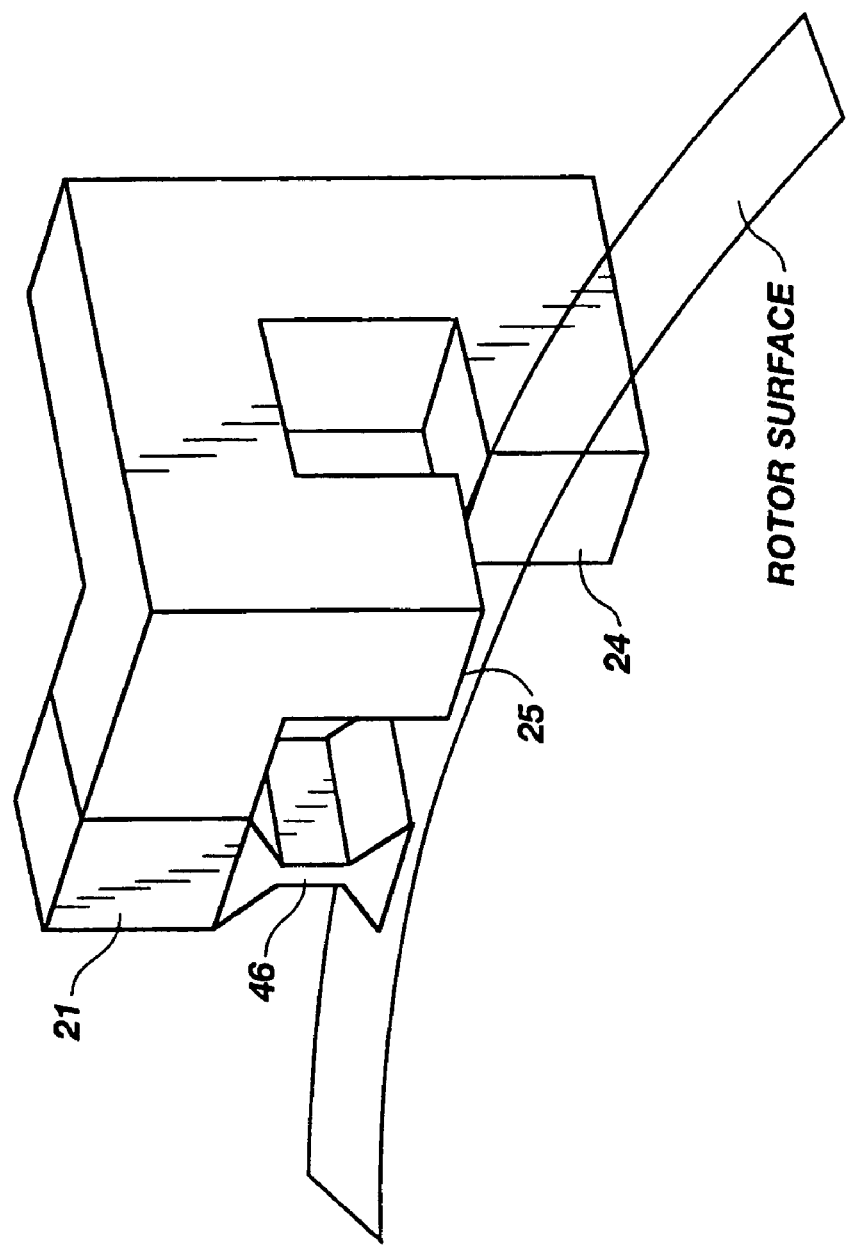
FIG. 16 shows a magnetic saturation link inserted into the PM circuit.

The present invention incorporates a magnetic saturation link 46 which is inserted into the PM circuit, as shown in FIG. 16. The saturation link 46 is a short section of the PM flux circuit which has a smaller cross sectional area than the other sections so that the magnetic flux density is at the magnetic saturation level of the soft iron material used in the flux path. The PM and the saturation link are sized so that the magnetic material in the saturation link is always saturated. This in turn keeps the PM magnetic flux density at a constant value when the EM rotor is off-center and minimizes the required lift-off force. Thus, the size of the EM coils can be minimized. This pattern is repeated over all of the PM magnetic flux paths in the ring design with a series of saturation flux links.

As will be appreciated, hemocompatibility is also of critical importance with blood pumps. There are three primary areas of concern for hemocompatibility in any blood pump: 1) hemolysis due to fluid shear, 2) thrombogenesis due to flow stagnation and/or fluid shear, and 3) material interactions with blood that result in thrombogenesis or complement activation. It is desirable to coat the fluid contacting surfaces of the pump with a coating that satisfies these concerns. It is also desirable to coat tissue contacting surfaces on implantable pumps with such a coating.

In the preferred embodiment, an amorphous coating of a transition metal nitride or other wear-resistant biocompatible ceramic material is applied according to a method disclosed in U.S. patent application Ser. No. 09/071,371, filed Apr. 30, 1998. By this method, a biocompatible, reliable, and durable room-temperature-processed amorphous coating can be provided on all blood-contacting and/or tissue contacting surfaces of the pump. A variety of biocompatible ceramic coatings may be applied by this method, including titanium nitride, silicon nitride, titanium carbide, tungsten carbide, silicon carbide, and aluminum oxide.

Titanium nitride is presently the preferred coating material. As a transition metal nitride, it is a well-known biomaterial. It is inert, fatigue resistant, biocompatible, corrosion resistant, and lightweight. In crystalline form it is presently used in tools and parts for high-temperature (up to 600° C.) applications as a corrosion and oxidation-resistant coating. Titanium nitride coatings have also been used as a wear resistance coating for orthopedic implants, on dental implants and instruments, and on defibrillator electrodes, where it is applied by chemical vapor deposition. However, all of these applications use titanium nitride in its crystalline form. Unfortunately, crystalline TiN cannot be applied to plastics, magnetic materials, and other heat-sensitive and flexible materials because of its high (~800° C.) coating temperature and because it chips when its substrate flexes.

Advantageously, the present invention incorporates the above-referenced process to provide an amorphous, room-temperature coating of TiN that can be applied to plastics, magnetic materials and other temperature-sensitive materials used in blood pumps or with other sensitive fluids. By this process, a TiN coating may be applied to pump surfaces by a magnetron sputtering technique in a vacuum chamber. Sputtering is a comparatively low-temperature technique by which titanium nitride (TiN) thin films can be uniformly deposited on substrates. Materials successfully coated by the inventors following this method include titanium, polyurethane, stainless steel, corethane, polyester, polyvinylchloride (PVC), iron plastic composite material, epoxy and Neodymium-iron-boron magnets. Some of these substrate materials were blood pump components. Following this method, the total thickness of the surface coat is about 1000 to 5000 angstroms. During more than 50 experiments, various substrates were tested to standardize the process conditions suitable for each substrate.

The preferred amorphous coating of TiN provides numerous advantageous features and benefits in this application. Such a coating provided by sputtering is applicable on cannulae and other flexing surfaces. Because this process provides a diffusion barrier, the surface inhibits permeability of gases and fluids into coated surfaces. Because it is deposited at room temperature, coating may be done without creating surface stresses and material damage on plastics, magnetic materials and composites. Because this technique is applicable to multiple materials (plastics, metals, composites), substrates of different materials can be coated with the same coating, and thus the entire fluid containment circuit can be coated with the same process and the same material. Finally, the surface is completely biocompatible, which allows the coating of all blood contacting surfaces and tissue contacting surfaces of blood pumps.

Those skilled in the art will appreciate that numerous modifications can be made without departing from the scope and spirit of the present invention. The appended claims are intended to cover such modifications.

We claim:

1. A blood pump comprising:
    a housing including a combination of permanent magnets and electromagnets positioned forming an electromagnetic bearing;
    an impeller disposed within said housing, said impeller being magnetically suspended with respect to the housing by magnetic flux generated by the combination of permanent magnets and electromagnets, and rotated by an electric motor,
    wherein the magnetic flux from the permanent magnet and the electromagnet shares a common magnetic path.

2. A blood pump as defined in 1, wherein the common magnetic path includes at least part of a soft iron structure within the electromagnet.

3. A blood pump as defined in 1, wherein the common magnetic path includes both radial and axial orientations with respect to an axis of rotation.

4. A blood pump as defined in 1, wherein the impeller is fully suspended along all axes of rotation.

5. A blood pump as defined in claim 1, wherein all blood-contacting surfaces are coated with a wear-resistant biocompatible ceramic coating.

6. A blood pump as defined in claim 5, wherein the ceramic coating is formed of a transition metal nitride.

7. A blood pump as defined in claim 5, wherein the coating is formed of a material selected from the group consisting of titanium nitride, silicon nitride, titanium carbide, tungsten carbide, silicon carbide, and aluminum oxide.

8. A blood pump as defined in claim 5, wherein the ceramic coating is amorphous and conductive.

9. A blood pump as defined in claim 1 which is configured for implantation in a human patient.

10. A blood pump as defined in claim 9, wherein all tissue contacting surfaces are coated with a wear-resistant biocompatible ceramic coating.

11. A blood pump as defined in claim 1, wherein the electromagnetic bearing defines a common magnetic path for flux generated by both permanent and electromagnet sources, said electromagnetic bearing including a first radial component and first axial component attached to the first radial component which collectively define at least a portion of the common magnetic path.

12. A blood pump as defined in claim 11, further comprising a second axial component coupled at a distal end of the first radial component, the combination defining at least a portion of the common magnetic path.

13. A blood pump as defined in claim 11, further comprising a second radial component coupled at a distal end of the first axial component, the combination defining at least a portion of the common magnetic path.

* * * * *